(12) United States Patent
Vogt et al.

(10) Patent No.: US 8,986,313 B2
(45) Date of Patent: Mar. 24, 2015

(54) MULTI-COMPONENT CARTRIDGE SYSTEM WITH SHIFTABLE CLOSURES IN THE CARTRIDGES

(71) Applicant: Heraeus Medical GmbH, Wehrheim (DE)

(72) Inventors: Sebastian Vogt, Erfurt (DE); Tim Schnieber, Frankfurt (DE)

(73) Assignee: Heraeus Medical GmbH, Wehrheim (DE)

( * ) Notice: Subject to any disclaimer, the term of this patent is extended or adjusted under 35 U.S.C. 154(b) by 206 days.

(21) Appl. No.: 13/682,051

(22) Filed: Nov. 20, 2012

(65) Prior Publication Data
US 2013/0138113 A1    May 30, 2013

(30) Foreign Application Priority Data
Nov. 25, 2011   (DE) .......................... 10 2011 119 357

(51) Int. Cl.
| A61B 17/58 | (2006.01) |
| A61B 17/60 | (2006.01) |
| A61F 2/00 | (2006.01) |
| A61B 17/88 | (2006.01) |
| B05C 17/005 | (2006.01) |

(52) U.S. Cl.
CPC ....... *A61B 17/8802* (2013.01); *B05C 17/00553* (2013.01); *B05C 17/00596* (2013.01); *B05C 17/0052* (2013.01); *A61B 2017/8838* (2013.01)
USPC .............................................. 606/93; 604/89

(58) Field of Classification Search
CPC .............................. A61B 17/8833; A61M 5/19
USPC .................. 604/89–91; 222/145.5; 606/92–94
See application file for complete search history.

(56) References Cited

U.S. PATENT DOCUMENTS

| 2,125,245 A | 7/1938 | McCray |
| 3,215,298 A | 11/1965 | Shaffer |

(Continued)

FOREIGN PATENT DOCUMENTS

| CH | 669164 A5 | 2/1989 |
| DE | 2 017 292 A1 | 10/1971 |

(Continued)

OTHER PUBLICATIONS

Japanese Examination Report for corresponding Japanese Application No. 2012-256913 dated Oct. 29, 2013.

(Continued)

*Primary Examiner* — Andrew Yang
(74) *Attorney, Agent, or Firm* — Norris McLaughlin & Marcus, P.A.

(57) ABSTRACT

A cartridge system for mixing and applying a mixing ware. The cartridges are arranged parallel and they are connected to a mixing space and an outlet opening. The cartridges each comprise a feed plunger for expelling starting components of the mixing ware from the cartridges through the openings, and each cartridge has at least one closure allocated to it that is shiftable in longitudinal direction of the cartridges, whereby the closures close the openings of the cartridges in a starting position, and the openings are open, at least in part, in an end position of the shiftable closures. In open position, the closure is shifted into a hollow space. The closures are cylindrical in shape and in their end position are capable of being lowered into cylindrical hollow spaces of the cartridges in order to uncover the openings.

14 Claims, 6 Drawing Sheets

(56) References Cited

U.S. PATENT DOCUMENTS

| | | | |
|---|---|---|---|
| 4,068,830 | A | 1/1978 | Gray |
| 4,690,306 | A | 9/1987 | Staeheli |
| 4,981,241 | A | 1/1991 | Keller |
| 4,989,758 | A | 2/1991 | Keller |
| 5,072,862 | A | 12/1991 | Keller |
| 5,137,182 | A | 8/1992 | Keller |
| 5,498,078 | A | 3/1996 | Keller |
| 5,968,018 | A | 10/1999 | Freeman et al. |
| 7,367,475 | B2 | 5/2008 | Hoerth et al. |
| 7,959,349 | B2 | 6/2011 | Sattig et al. |
| 8,177,099 | B2 | 5/2012 | Suchan et al. |
| 2003/0179648 | A1 | 9/2003 | Heusser et al. |
| 2007/0051750 | A1* | 3/2007 | Suchan et al. ............... 222/137 |
| 2008/0203112 | A1* | 8/2008 | Peuker et al. ............... 222/137 |
| 2008/0304355 | A1 | 12/2008 | Sattig et al. |
| 2009/0062808 | A1 | 3/2009 | Wolf, II |
| 2009/0105144 | A1 | 4/2009 | Vogt et al. |
| 2009/0105366 | A1 | 4/2009 | Vogt et al. |
| 2009/0308891 | A1 | 12/2009 | Bublewitz et al. |
| 2011/0272436 | A1 | 11/2011 | Vogt et al. |

FOREIGN PATENT DOCUMENTS

| | | |
|---|---|---|
| DE | 3 440 893 A1 | 5/1986 |
| DE | 10 2005 041 961 A1 | 3/2007 |
| DE | 102005041962 B3 | 3/2007 |
| DE | 10 2007 044 983 A1 | 4/2009 |
| DE | 10 2007 052 116 A1 | 4/2009 |
| DE | 10 2007 050 762 | 5/2009 |
| DE | 10 2008 030 312 A1 | 1/2010 |
| DE | 10 2010 019 217 A1 | 11/2011 |
| EP | 0 236 129 A2 | 9/1987 |
| EP | 0 261 466 A1 | 3/1988 |
| EP | 0 289 882 A1 | 11/1988 |
| EP | 0 294 672 A1 | 12/1988 |
| EP | 0 431 347 A1 | 6/1991 |
| EP | 0 607 102 A1 | 7/1994 |
| EP | 0 664 153 A1 | 7/1995 |
| EP | 0 693 437 A1 | 1/1996 |
| EP | 0 787 535 A1 | 8/1997 |
| EP | 1430959 A2 | 6/2004 |
| EP | 1 799 335 | 6/2007 |
| EP | 2 008 707 A1 | 12/2008 |
| GB | 1 188 516 | 4/1970 |
| JP | 2009506798 A5 | 2/2009 |
| JP | 2009529377 A5 | 8/2009 |
| JP | 2010105728 A | 5/2010 |
| JP | 2011235102 A | 11/2011 |
| JP | 2011235961 A | 11/2011 |
| WO | 2005016170 A2 | 2/2005 |
| WO | 2006 005206 A1 | 1/2006 |
| WO | 2007104037 A2 | 9/2007 |
| WO | 2010 006455 A1 | 1/2010 |

OTHER PUBLICATIONS

European Examination Report for corresponding European Application No. 12007468.7 dated Nov. 13, 2013.

Canadian Office Action for corresponding Canadian Application No. 2,794,515 dated Jan. 21, 2014.

English-language Translation of Japanese Examination Report for corresponding Japanese Application No. 2012-256913 dated Sep. 2, 2014.

* cited by examiner

MULTI-COMPONENT CARTRIDGE SYSTEM WITH SHIFTABLE CLOSURES IN THE CARTRIDGES

This application claims priority to DE 10 2011 119 357.3 filed on Nov. 25, 2011.

BACKGROUND OF THE INVENTION

The invention relates to cartridge systems for mixing and applying a mixing ware, in particular a medical cement, comprising at least two cartridges that are arranged parallel to each other and a mixing space having an outlet opening, whereby the cartridges each comprise in the cartridge walls at least one opening that connects the cartridges to the mixing space, the cartridges each comprise a feed plunger for expelling starting components of the mixing ware from the cartridges through the openings, and each cartridge has at least one closure allocated to it that is shiftable in longitudinal direction of the cartridges, whereby the closures close the openings of the cartridges in a starting position, and the openings are open, at least in part, in an end position of the shiftable closures.

Cartridge systems for mixing and applying a mixing ware can consist of multiple components and are to ensure safe storage and safe closure for components in at least two cartridges prior to their use. The cartridge system should be safe and easy to open right before the application of the mixing ware, whereby synchronous opening of the individual cartridges is desirable.

Reactive pasty two- or multi-component systems must be stored separately after their production and until their application in order to prevent premature, inadvertent reactions of the components. Cartridge systems for the application of pasty two- or multi-component systems have been known for decades. The following documents are cited for exemplary purposes, CH 669 164 A5, EP 0 607 102 A1, EP 0 236 129 A2, DE 3 440 893 A1, U.S. Pat. No. 4,690,306 A, US 2009/062808 A1, EP 0 787 535 A1, WO 2006/005 206 A1, EP 0 693 437 A1, EP 0 294 672 A, EP 0 261 466 A1, and EP 2 008 707 A1. After filling the cartridges with reactive pastes, the cartridges need to remain safely closed until their application. The pasty two- or multi-component systems are mixed right before their application, usually through the use of static mixers. The following documents are cited for exemplary purposes, GB 1,188,516 A, U.S. Pat. No. 2,125,245 A, U.S. Pat. No. 5,968,018 A, U.S. Pat. No. 4,068,830 A, US 2003/179648 A1, EP 1 799 335 A1, EP 0 664 153 A1, and EP 0 289 882 A1. In this context, mobile plungers, which are also used to dispense the cartridge content, usually seal the cartridge floors.

A number of solutions for closing the cartridge system have been proposed.

One simple, but very effective, principle is to close the cartridge system with a closure that can be rotated (EP 0 431 347 A1, DE 2 017 292 A1, U.S. Pat. No. 3,215,298 A). The closure is unscrewed prior to the application. Subsequently, a dispensing tube is screwed into a thread on the cartridge system or fixed through a peg system that simulates a thread. This is disadvantageous in that the user needs to perform rotational motions twice until the paste material can be expelled. Moreover, the closure may be screwed out and the dispensing tube is attached only later. In the interim between the cartridges being opened and the dispensing tube being inserted, ingredients of the pastes may evaporate, especially if the pastes contain volatile substances.

The closure that is in very common use currently in the adhesives and sealant industry is based on the wall material of the cartridge head being provided to be very thin at the cartridge head such that said wall can be perforated easily. During perforation, particles become detached from the wall and can thus enter the pasty material.

The backside of the cartridges is usually closed by mobile plungers that are designed for expelling the pastes during application. In the case of humidity- and air-sensitive pastes, aluminium cartridges may be used that are closed by plastic plungers and over which aluminium cylinders that are closed on one side are pressed in for sealing purposes. During the application of the pastes, the aluminium cylinder having one closed side is moved jointly with the plunger towards the front in the direction of the cartridge head through the action of cartridge applicator guns and the paste is expelled in the process. However, any contact of paste and aluminium surfaces may be problematic in medical applications.

A cartridge system is based on packaging pasty multi-component systems in tubular bags (WO 2010/006455 A1). This involves inserting the sealed tubular bags into cartridges. Tubular bags are advantageous in that they are suitable for packaging pastes that contain volatile ingredients. Tubular bags made of compound materials, such as aluminium compound bags, are particularly well-suited for this purpose. The tubular bags are opened by blades that rotate along when the dispensing tube is being screwed in. The bags are cut open in the course of the rotational motion of the blades and openings in the cartridges for dispensing the content are thus provided. The pasty bag content is subsequently squeezed through these openings in the cartridges in the direction of the static mixer.

In this context, it is disadvantageous that packaging pasty materials in tubular bags and, in addition, in cartridges is quite expensive and reserved for special applications only. Moreover, it is a problem in many applications, especially in the field of medicine, that parts of the cut tubular bags may become detached and thus may enter into the pasty components and thus contaminate the mixing ware.

Using cartridge systems for sterile pasty medical products, there is a need for not only the pastes, but obviously the cartridges and secondary packaging means also to be provided in sterile form to the user. For example after aseptic filling of the previously sterilised cartridges, these may be transferred directly to sterile packaging means. Moreover, it may make sense for certain products to sterilise the surfaces of filled cartridges jointly with the packaging means after packaging is completed. Aside from gamma sterilisation, which cannot be used with paste systems that can be polymerised, there is the option to use ethylene oxide gas for sterilisation.

However, one issue of said sterilisation with gas in the case of paste systems containing monomers with a high vapour pressure is that a fraction of the monomers in the cartridges evaporates after the actual sterilisation, when the residual ethylene oxide is removed by the action of a vacuum, whereby the monomers form a gas phase in the cartridges and can thus exert a pressure against the plungers. This means that the feed plungers are moved in the direction of the cartridge floors in undesired manner and may be expelled from the cartridges in the extreme case such that the pastes may leak out.

Polymethylmethacrylate bone cements have been in use in medicine for decades for permanent mechanical fixation of total joint endoprostheses. They are based on powder-liquid systems. Recently, polymethylmethacrylate bone cements that are based on the use of cement pastes have been proposed as well (DE 10 2007 050 762 A1, DE 10 2008 030 312 A1, DE 10 2007 052 116 A1). Thus far, no suitable cartridge systems have been proposed for said cements.

With regard to the application of bone cements for fixation of total joint endoprostheses, it is always necessary to take into consideration that the OR staff is under time pressure during these surgeries. Therefore, as a matter of principle, cartridge systems for medical applications involving the application of paste-like polymethylmethacrylate bone cements should be designed such that they are largely resistant to user errors and can be operated rapidly and safely even in stressful situations.

The methylmethacrylate monomer is an essential ingredient of paste-like polymethyl-methacrylate bone cements. Said monomer evaporates readily and has a relatively high vapour pressure at room temperature. For this reason, it is essential to note with regard to the use of methylmethacrylate-containing pastes that the feed plungers in the cartridges may be moved and may be expelled from the cartridges in the extreme case by the evaporating methylmethacrylate upon exposure to a vacuum, such as during the degassing as part of ethylene oxide sterilisation.

A cartridge system for mixing and applying a mixing ware is known from DE 10 2010 019 217 A1. The cartridge system comprises at least two cartridges and a mixing space that is connected to the cartridges through one opening each. The cartridges have feed plungers for expelling the starting components arranged in it. A shiftable closure that closes the openings is arranged in the mixing space. When a dispensing tube is screwed-in, the closure is shifted in the mixing space and the openings are thus uncovered.

This is disadvantageous in that only the cartridges are opened initially and the cartridge contents (starting components) are dispensed only later. In the meantime, the cartridge content may be subject to change or deterioration. Moreover, it is not possible to see from outside whether or not the cartridge system is already open.

A cartridge system of this type is known from DE 10 2007 044 983 A1. The cartridge system comprises a shiftable valve for each cartridge that covers an opening in the cartridge. By applying pressure by means of a feed plunger, the valve is shifted and the opening is uncovered. The valve is situated, as a ring, on a peg at the front end of the cartridge system.

This is disadvantageous in that the structure of the valve is complex and thus expensive. Another disadvantage is that, as before, it is not easily possible to recognise from outside whether or not the closure is already open. Basically, there is always a need for further simplification of the structure of cartridge systems of this type. The structure requires the feed-through of the starting components and of the mixing ware to have relatively small cross-sections which lead to a high resistance upon dispensation of the cartridge content. Moreover, the air needs to be displaced from the valve system. In this context, the valve system includes a dead space that is not available for storage or for mixing of the components.

BRIEF SUMMARY OF THE INVENTION

It is the object of the present invention to overcome these and other disadvantages that have not been specified above. In particular, a cartridge system is to be provided that is easy and inexpensive to manufacture, but at the same time ensures that the cartridges can be opened safely and easily. Safe storage and safe closure of paste-like components in at least two cartridges prior to their use should be ensured. The cartridge system should be safe and rapid to open right with minimal effort right before application of the pastes in order to render the application during surgeries easy and thus reduce and/or overcome the shortcomings of existing cartridge systems and their closure systems. Accordingly, a closure system is to be developed that safely closes cartridges for multiple components and allows the individual cartridges to be opened rapidly and without difficulties. Another aim was [to develop] a closure system that can be manufactured entirely from inexpensive plastic injection moulded parts.

Said objects are met in that at least two cartridges each comprise a cylindrical hollow space and in that the closures are arranged on the inside of the cartridges, whereby the closures are cylindrical in shape and can, in their end position, be lowered into the cylindrical hollow spaces of the cartridges in order to uncover the openings.

According to the invention, the starting components are preferably pasty masses, and components of medical cements are particularly preferred.

A cylindrical shape shall be understood to mean any body having a base surface that corresponds to the cross-section of the body at any height, preferably perpendicular to the base surface. Accordingly, a cylindrical shape is bordered through two parallel, planar surfaces (base and top surface) and a jacket or cylinder surface formed through parallel straight lines. This means that is is generated through shifting a planar surface or curve along a straight line that is not positioned in said plane. A cylinder having a circular, oval or rounded base surface is a particularly preferred form of said cylinder.

In this context, the invention can provide that the cylindrical hollow spaces of the cartridges are connected to the surroundings through at least one ventilation opening such that the air can escape from the hollow space when the closure is being lowered, whereby the hollow spaces preferably are arranged in the frontal region of the cartridge system and the ventilation openings are arranged in cartridge heads of the cartridges.

The frontal region of the cartridge system is the region, in the direction of which the feed plungers are moved in order to expel the starting components from the cartridges. The cartridge heads form the front end of the cartridges.

According to the invention, it is particularly preferred for the hollow spaces to be bordered on the front through the cartridge heads, whereby in particular the distance of the opening to the cartridge heads plus the cross-section of the opening in longitudinal direction of the cartridge is larger than the height of the corresponding cylindrical closures in the corresponding cartridge. Preferably, the height of the cylindrical closures in the cartridges corresponds to the distance of the opening in the cartridge from the cartridge head of said cartridge. This ensures that the closures, in their lowered end position, uncover the openings, preferably uncover them fully or almost fully.

A further embodiment of the invention can provide the closures to separate preferably separate in a tight manner, particularly preferably separate in a fluid-tight and/or gas-tight manner, the hollow spaces from the cartridge regions filled with the starting components. Even more particularly preferably, the closures separate the hollow spaces from the cartridge regions filled with the starting components in a pressure-tight manner.

What said separation achieves is that the starting components cannot be pushed through between the closures and the internal cartridge walls into the hollow space and preferably no air from the hollow space mixes with the starting components when a pressure is applied to the feed plungers.

Moreover, the invention can provide that the shiftable closures are arranged in the cartridges in a press-fit.

This measure also renders the cartridges leak-proof. Regarding the press-fit, it is important to make sure that the feed plungers and the closures can still be moved manually. If the press-fit is adequate, there is no need to have additional seals. The invention can just as well provide the feed plungers to also be arranged in the cartridge in a press-fit.

Moreover, the invention can provide the closures to be compact bodies or hollow bodies, in particular hollow cylinders having at least one closed base surface.

This structure is particularly easy and inexpensive to implement. Moreover, the cartridge systems are also particularly easy to assemble then.

According to another particularly preferred embodiment of the invention, the hollow spaces can have an internal diameter that is equal to or larger than the external diameter of the corresponding closure, and/or the hollow spaces are of a length of at least one-tenth of the height of the closure.

At said dimensions, the closure can be lowered well in the hollow space and a sufficient shifting path for the closure is ensured in order to implement openings having a sufficient cross-sectional area in their open state for pressing the starting components through.

Cartridge systems according to the invention can just as well be characterised in that each cartridge has at least one blocking organ arranged in it that limits the axial motion of the closure above the outlet opening.

The blocking organ can be a simple limit stop or any other variation of the cross-section of the internal cartridge space, or one or more pegs.

Moreover, the invention can provide that the feed plunger in each cartridge is connected in a non-positive fit-like manner to the closure of said cartridge by means of the starting component arranged in said cartridge such that a force acting on the feed plungers can be transferred to the closures and the closures can be transitioned from the starting position to the end position.

Said structure allows the openings and/or the cartridge system to be opened and the mixing ware to be mixed and applied by means of pressing onto the feed plungers. Accordingly, one type of actuation or one working step is sufficient to open the cartridge system and mix and apply the mixing ware.

Another particularly preferred embodiment of the invention can provide the feed plungers and closures to be arranged in pairs each in a tube, which contains between them one starting component each, whereby the closed tubes are arranged in the cartridges, in particular behind the openings as seen from the cartridge head.

Said structure allows an unfilled structural component for cartridge systems with various fillings to be manufactured. Various starting components are then combined through inserting the tubes which can be filled with different starting components. Said measure allows the manufacturing to be designed more variable.

Another embodiment of the invention can provide at least one closure to have an optical indicator arranged on it by means of which the starting position can be visually differentiated from the end position by means of at least one inspection opening and/or one inspection window in at least one cartridge, in particular by means of at least one inspection opening and/or one inspection window in at least one of the cartridge heads, and/or which projects from the cartridge through said at least one inspection opening when the closure is in the end position, whereby the inspection opening preferably also serves as the ventilation opening.

The invention can provide an optical indicator each that is attached at the external end of a closure that is provided as closure plunger and is visually recognisable after axial motion of the closure plunger in the direction of the cartridge heads through at least one opening in the cartridge heads or that is exited from the cartridge through said at least one opening. The optical indicator allows the user to recognise if the cartridges are opened through shifting of the closure plunger.

Accordingly, this allows the user to recognise directly whether or not the cartridge system has been used already. The use of a previously used cartridge system during surgeries is easy to check and can be avoided easily which saves valuable time.

The invention can just as well provide the mixing space to be connected to a dispensing tube having a static mixer either in fixed or detachable manner, whereby the static mixer preferably extends into the mixing space.

The dispensing tube facilitates the application of the mixing ware and the static mixer improves the mixing of the mixing ware.

Another particularly preferred embodiment of a cartridge system according to the invention can be implemented through providing that a rotatable locking device is supported like in a bearing in a bracket in the region of the cartridge heads such as to be rotatable, whereby the locking device is a rotationally symmetrical body having at least one cylindrical recess, preferably having one recess for each cartridge, whereby the locking device, or at least regions of it, forms at least one cartridge head and the recess of the locking device, in a first position, forms at least one part of one of the hollow spaces for accommodating the closure such that the closure of said cartridge can be lowered into the hollow space in said first position and cannot be lowered into the hollow space in a second, rotated position of the locking device.

Preferably, the cylindrical recesses are arranged to be perpendicular to the symmetry axis of the rotationally symmetrical body. Only the base body of the locking device is a rotationally symmetrical body. The symmetry of the locking device is broken through the recesses and any further lead-throughs and/or openings for pressing-though the starting components or mixing ware, and/or serving as ventilation openings and/or inspection windows.

The transition between the first and the second position is effected through rotating the locking device. The rotation axis in this context is the symmetry axis of the rotationally symmetrical body of the locking device. Preferably, the rotation axis is arranged to be perpendicular to the longitudinal axis of the cartridges.

Even though this embodiment necessitates an unlocking of the cartridge system and thus an additional working step, it provides the advantage that inadvertent opening of the cartridge system by means of pressing on the feed plungers unintentionally is prevented. The locked position of the locking device is the second position and the ready-for-use position of the locking device is the first position. In the ready-for-use first position, the closures can be lowered into the hollow spaces, whereas this is not feasible in the locked second position.

Moreover, the invention can provide a dispensing tube to be arranged on the locking device and, in the first position, to be connected to the mixing space by means of the locking device, whereby the outlet opening of the mixing space is preferably closed through the locking device being in the second position.

A multi-component cartridge system according to the invention having cartridges that are arranged to be parallel to each other and each contain a pasty substance and are connected irreversibly or reversibly to a dispensing tube having a static mixer can be implemented, for example, in that a) each cartridge is closed (at the cartridge floor) through at least one feed plunger that can be shifted in axial direction;

b) each cartridge possesses at the cartridge head at least one opening that is arranged to be perpendicular to the longitudinal axis of the cartridge;

c) the opening or openings of each cartridge is or are closed through at least one axially shiftable closure plunger, whereby the opening or openings can be uncovered through shifting the closure plunger or closure plungers;

d) the cartridges are connected to each other in such manner that they form a mixing space that is closed in the direction of the cartridge floors;

e) the opening or openings connect(s) the interior space of the cartridges to the mixing space;

f) the mixing space is patently connected to the dispensing tube in irreversible or reversible manner;

g) a hollow space is present at each cartridge head above the opening or openings and has an internal diameter that is equal to or larger than the external diameter of the closure plunger, and which has a length of at least one-tenth of the height of the closure plunger;

h) each cartridge head has at least one blocking organ arranged on it that limits the axial motion of the closure plunger above the opening or openings; and i) the feed plunger in each cartridge is connected to the closure plunger in a non-positive fit-like manner through the pasty substance that is arranged in the cartridge.

According to the invention, the closures can be provided as closure plungers.

Another variant of an embodiment of the invention can provide one feed plunger and one closure plunger each to be arranged in a tube that contains a pasty substance as starting component, whereby said closed tube is arranged below the outlet opening in the cartridge. This means that the tube containing the feed plunger and the closure plunger forms the primary packaging means of the pasty substance. Said primary packaging means is to be inserted into the cartridges. This allows for separate filling processes of very different starting components, which can be combined with each other in any desired way in the multi-component cartridge. By this means, very different combination of pasty bone cements containing or not containing antibiotics can be packaged.

The invention is based on the surprising finding that simple cylinders as shiftable closures in the cartridges can be used to close openings allowing starting components of a mixing ware to be pressed through, whereby the closures can be lowered into hollow spaces of the cartridges in order to open the cartridge system and render it ready for use. Some of the benefits of the invention are in the simplicity of this design. Simultaneously, the present invention allows a cartridge system to be implemented in which the cartridge system is opened by means of the same pressure that acts on the feed plungers also being used to mix and expel the mixing ware or the starting components from the cartridges into the mixing space.

Applying the invention allows a multi-component cartridge system to be provided, in which the individual cartridges are opened automatically and synchronously upon the application of pressure onto the feed plungers.

BRIEF DESCRIPTION OF THE DRAWINGS

Exemplary embodiments of the invention shall be illustrated in the following on the basis of six schematic figures, though without limiting the scope of the invention. In the figures.

DETAILED DESCRIPTION OF THE INVENTION

Figure 1:
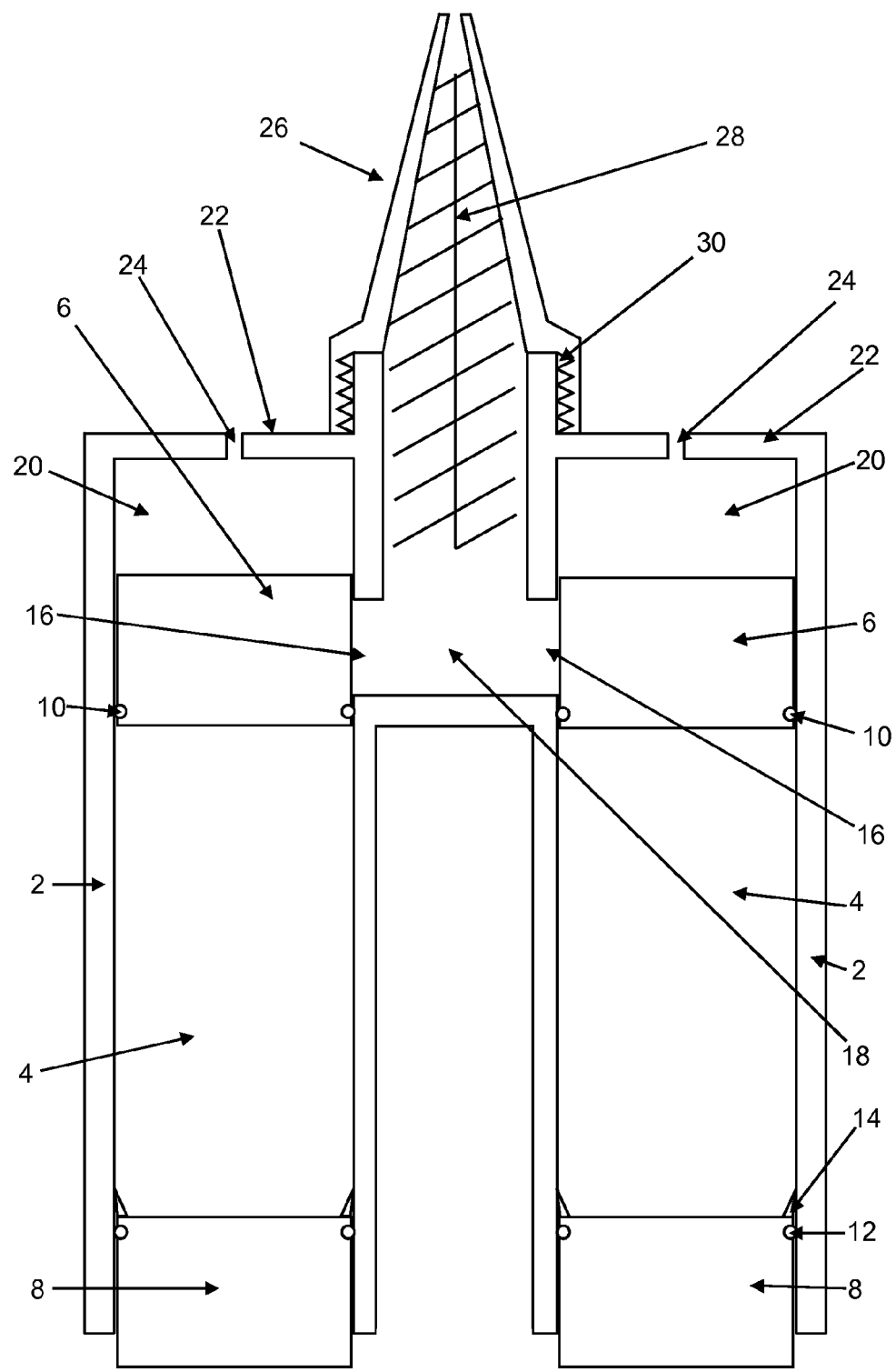
FIG. 1: shows a schematic cross-sectional view of a cartridge system according to the invention having closed openings to the mixing space.

FIG. 1 shows a schematic cross-sectional view of a cartridge system according to the invention having two cartridges 2. The cartridges 2 form cylindrical interior spaces. The insides of the cartridges 2 contain starting components 4 for a mixing ware to be mixed. The starting components 4 can, for example, be pasty masses and are preferably intended for forming a medical cement as mixing ware. The regions of the cartridges 2, which contain the starting components 4, are bordered in the front (on the top in all figures) through one closure 6 each and closed on the back through one feed plunger 8 each. The closures 6 have the same cylindrical geometry as the insides of the cartridges 2 and are arranged in the inside spaces of the cartridges (2) such as to be sealed through seals 10 that surround the entire circumference of the closures 6. The feed plungers 8 also have the same cylindrical geometry as the inside spaces of the cartridges 2 and seal the same through seals 12. The seals 12 also surround the entire circumference of the feed plungers 8.

Both the feed plungers 8 and the closures 6 are arranged such as to be mobile along the longitudinal axis of the cartridges 2 (from bottom to top or vice versa in all figures). The starting components 4 are incompressible masses. When a force is applied to the feed plungers 8 and drives the same more deeply into the inside of the cartridges 2, this leads to the force being hydraulically transmitted to the closures 6 by means of the starting components 4. To ensure that the feed plungers 8 can be moved synchronously only, these can be connected to each other in fixed manner. The feed plungers 8 have stripping lips 14 arranged on them which serve to ensure that as much as possible of the starting components 4 can be pressed to the front by means of the feed plungers 8.

The closures 6 close openings 16 which connect the inside of the cartridges 2 to a mixing space 18. On the front of the cartridges 2, the inside space of the cartridges 2 is formed by a hollow space 20 each that is closed on the front through a cartridge head 22. The cartridge floor of the cartridge system that is formed through the feed plungers 8 in the starting state is situated opposite from the cartridge head 22. The cartridge head 22 has a ventilation opening 24 situated in it by means of which the hollow space 20 is connected to the surroundings.

The mixing space 18 is opened in the front through an outlet opening, whereby a dispensing tube 26 is arranged on the mixing space 18 and/or on the outlet opening of the mixing space 18. A static mixer 28 that extends all the way to the mixing space 18 is arranged in the dispensing tube 26. When the starting components 4 are pressed from the cartridges 2 through the openings 16 into the static mixer 28, the starting components get mixed through the static mixer 28 in order to obtain a well-mixed mixing ware that can be applied subsequently. The dispensing tube 26 is screwed-on on the front of the cartridge system through a thread 30.

FIG. 1 shows the closures 6 in the starting position, in which the openings 16 are closed through the closures 6. A pressure applied to the feed plungers 8 is transmitted to the closures 6 by means of the at least largely incompressible starting components 4. This pushes the closures 6 into the hollow spaces 20. Air can escape from the hollow spaces 20 through the ventilation openings 24. The motion of the closures 6 uncovers the openings 16.

Figure 2:
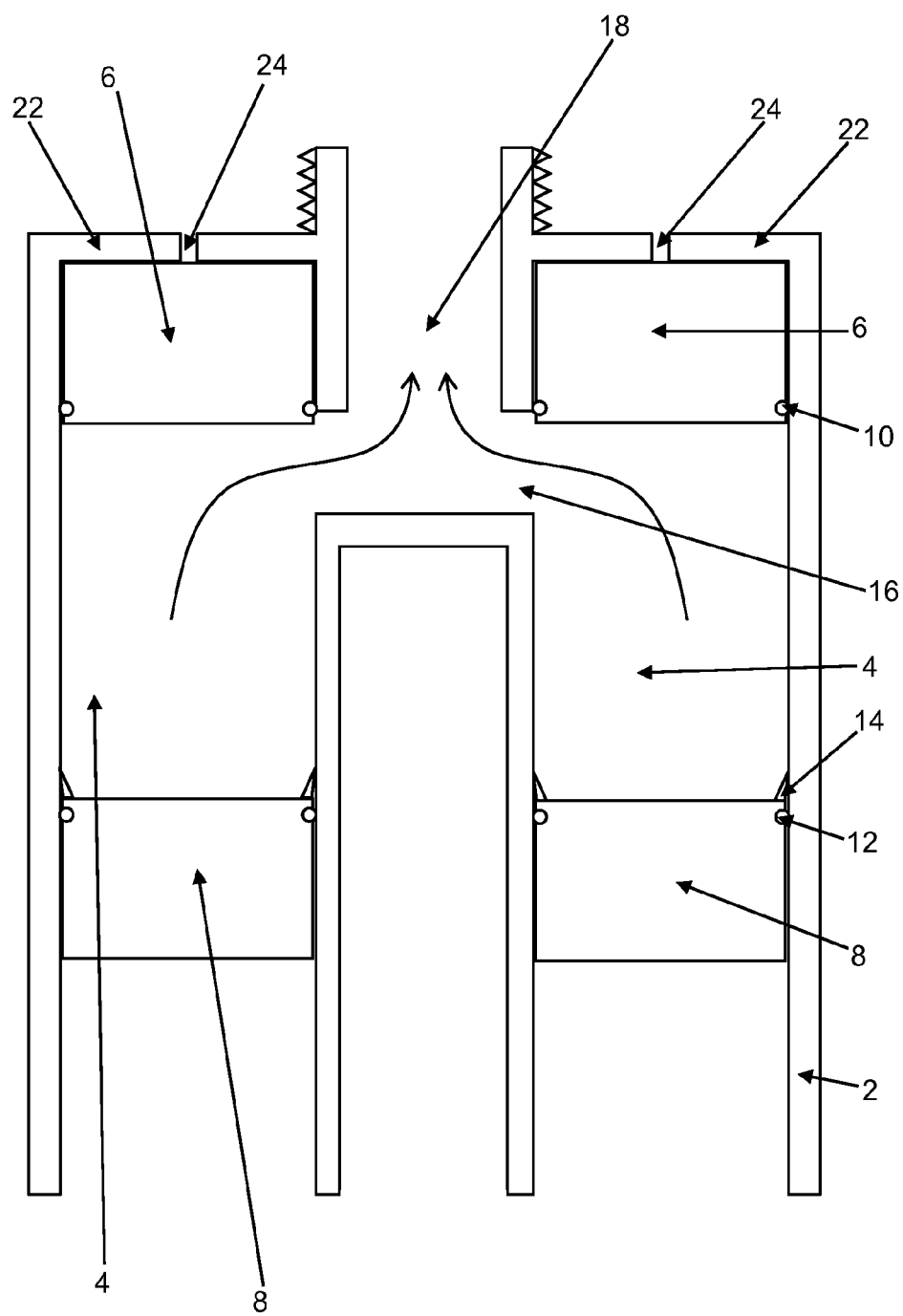
FIG. 2: shows a schematic cross-sectional view of a cartridge system according to the invention having open openings to the mixing space.

The open situation is shown in FIG. 2, in which a schematic cross-sectional view of the cartridge system according to the invention having open openings 16 to the mixing space 18 is shown. The closures 6 are situated in the end position or in the open position therein. The pressure acting on the feed plungers 8 then causes the starting components 4 for the mixing ware to be pressed through the openings 16 into the mixing space 18 and then from the mixing space 18 through the outlet opening.

Figure 3:
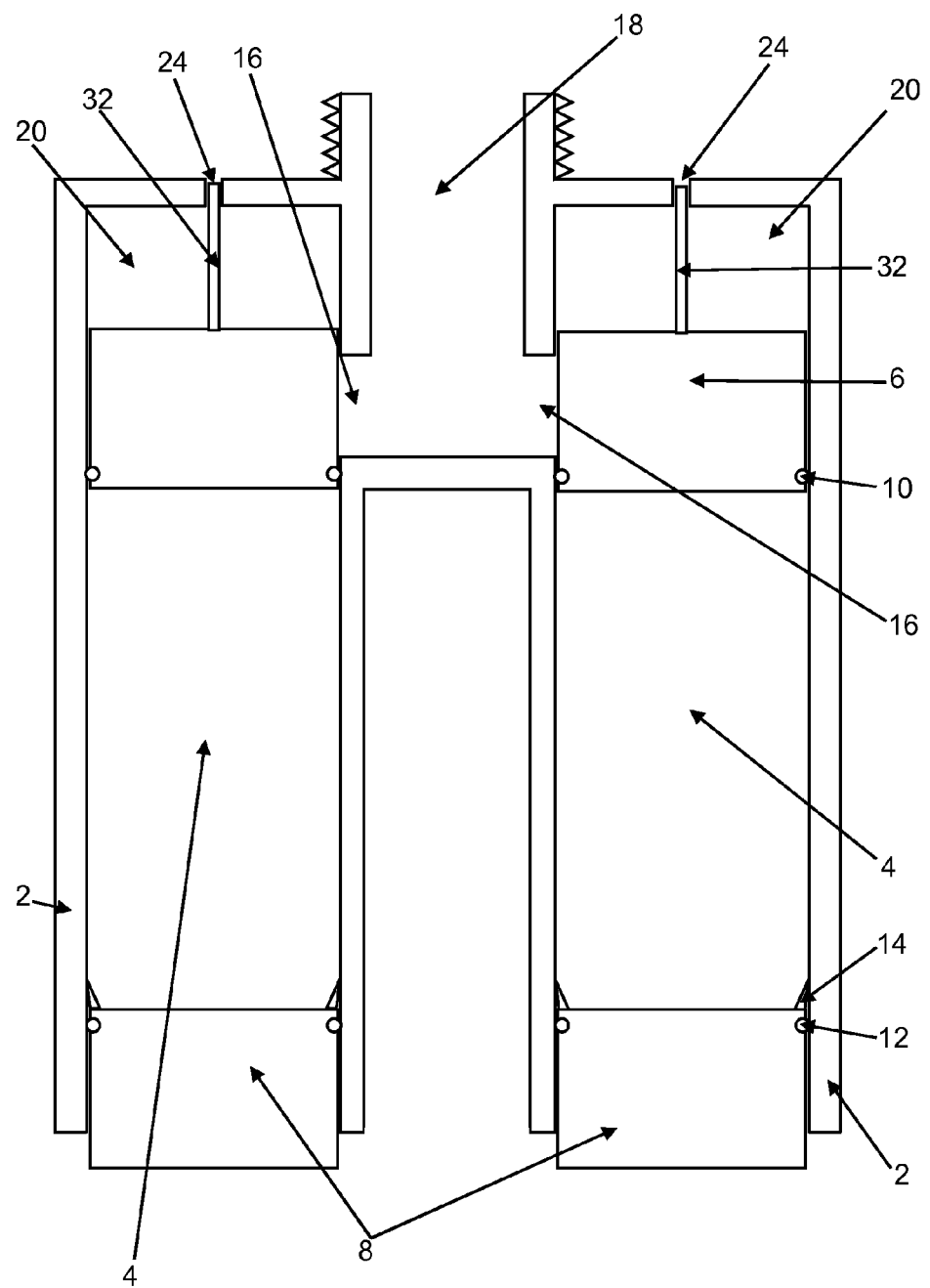
FIG. 3: shows a schematic cross-sectional view of a closed cartridge system according to the invention having an indicator.
Figure 4:
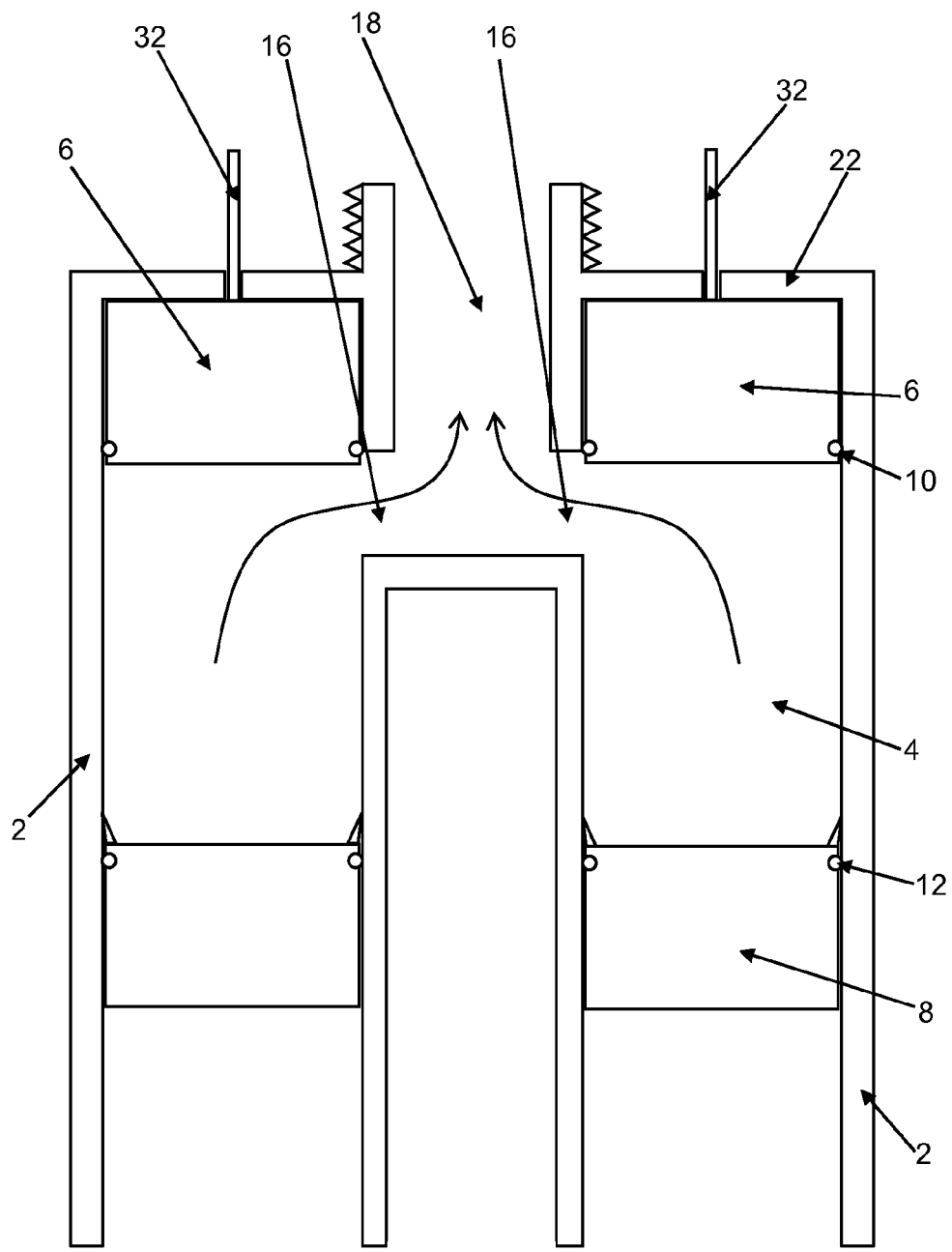
FIG. 4: shows a schematic cross-sectional view of an open cartridge system according to the invention having an indicator.

For reasons of simplicity, FIGS. 2, 3, and 4 show the structure while omitting the dispensing tube 26 having the static mixer 28. The mixing space 18 is open in the front in the region of its outlet opening. It is also not obligatory that the dispensing tube 26 needs to be screwed-on, but it can just as well be connected to the mixing space 18 through a locking device or be provided as the same part as the mixing space 18.

The starting components 4 are mixed in the mixing space 18 and are pressed through the dispensing tube 26 where they are mixed well by means of the static mixer 28. The flow of the starting components 4 from the cartridges 2 through the openings 16 and through the mixing space 18 is shown by means of the curved arrows in FIG. 2 and FIG. 4. Accordingly, the same force that serves to open the openings 16 through lowering the closures 6 into the hollow spaces 20 is also used to dispense and mix the starting components 4 such that the cartridge system can be made ready-for-use and can be applied in one working step.

At the same time, the structure is very simple. All parts can be manufactured through simple injection moulding techniques from plastic materials and are easy to assemble. The closure 6 can be a simple cylinder that can just as well be provided to be hollow. Accordingly, the cartridge system shown here is easy to operate and simultaneously has simplest and therefore inexpensive structure.

The upper side of the closures 6 or the entire closures 6 can be provided in a colour that has a stark contrast to the external colour of the cartridge system. What this achieves is that the closures 6 being in the end positions can be recognised easily through the ventilation openings 24. The contrast is then an indicator of the status of the cartridge system. By this means, it can be recognised easily from outside whether or not the cartridge system has already been used.

An indicator 32 that is even more easily recognised is shown in an embodiment according to FIGS. 3 and 4, which show a schematic cross-sectional view of a cartridge system according to the invention in open and closed state. The indicator 32 is provided in the form of a small rod that is arranged on the front of the closures 6 and extends into (FIG. 3) or through (FIG. 4) the ventilation openings 24. Preferably, the indicator 32 has a signal colour, as before, for example red or orange, with a good contrast to the remaining exterior of the cartridge system, in particular the outside of the cartridge heads 22.

The indicator 32 should either have a smaller diameter than the ventilation openings 24 such that air can escape from the hollow space 20 through the remaining gaps in the ventilation openings 24 or further ventilation openings (not shown) are provided through which air can escape from the hollow space 20. The effect of ventilating the hollow space 20 is that no force needs to be exerted by means of the feed plungers 8 against the pressure that is building up in the hollow space 20.

However, the invention can just as well provide that no ventilation openings are provided such that the compressed air in the hollow spaces 20 effects a restoring force that propels the closures 6 back to the starting position or leads to closure of the openings 16 when no force from outside is exerted on the feed plungers 8 any longer. For this purpose, spring elements (not shown) can be arranged in the hollow spaces 20 just as well. However, single use with ventilation openings 24 is preferred.

In the open state of the closures 6, the indicators 32 project from the ventilation openings 24 and are easy to see.

Figure 5:
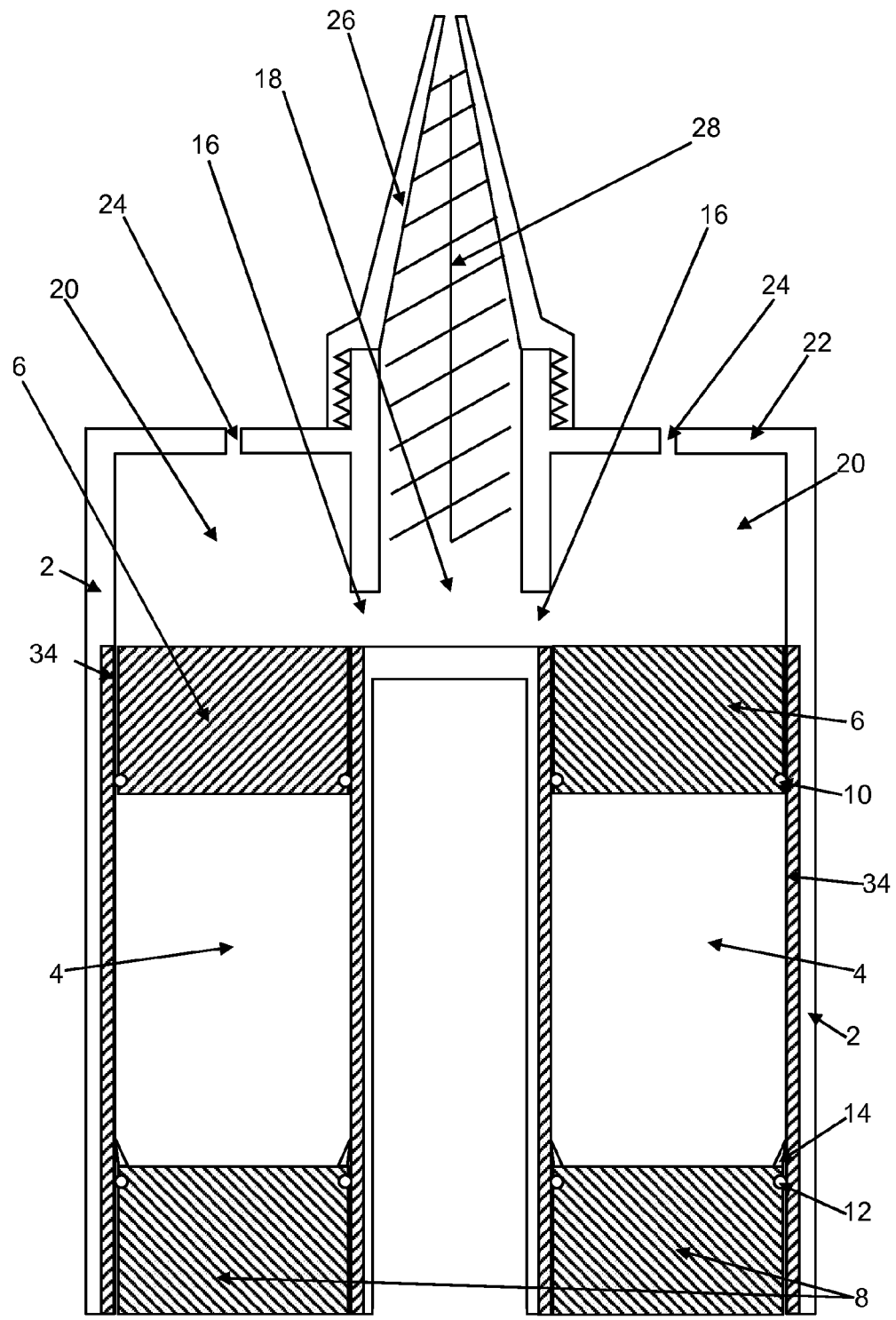
FIG. 5: shows a schematic cross-sectional view of a cartridge system according to the invention having inserted tubes.

FIG. 5 shows a schematic cross-sectional view of another exemplary embodiment of an alternative cartridge system according to the invention, in which tubes 34 are plugged into the cartridges 2. The tubes 34 contain the feed plungers 8 and the closures 6 as well as the starting components 4. For manufacturing of the cartridge system, various tubes 34 containing different starting components 4 can be combined and inserted into a pre-manufactured standard part.

The inserts comprising the tubes 34 are shown hatched in FIG. 5. Accordingly, the advantage of said system is the further simplification of the manufacturing of cartridge systems according to the invention. In all other aspects, the functional principle remains the same. The closures 6 are pressed forward past the openings 16 into the hollow space 20 through exerting a force on the feed plungers 8. This generates a connection between the inside of the tubes 34 containing the cartridge content 4 (i.e. the starting components 4) and the mixing space 18 by means of the openings 16. The starting components 4 are pressed through the openings 16 into the mixing space 18 and then mixed therein. Subsequently, the static mixer 28 provides for additional mixing of the starting components 4, and the mixing ware can subsequently be applied through the dispensing tube 26. For example, a ready-made bone cement could be applied during a surgery by this means.

Figure 6:
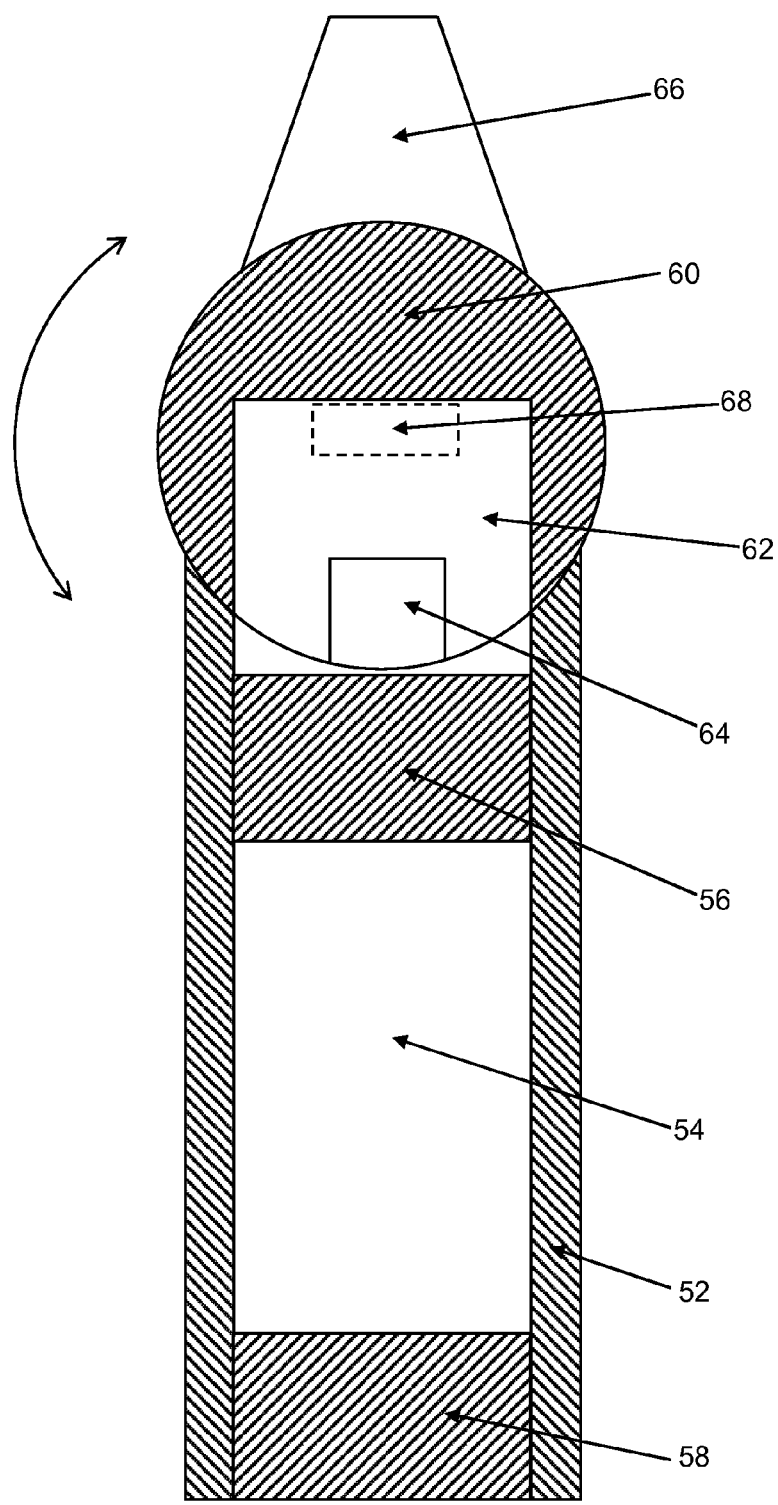
FIG. 6: shows a schematic cross-sectional view of a closed cartridge system according to the invention having a locking device that can be rotated.

FIG. 6 shows a schematic cross-sectional view of another cartridge system according to the invention in the closed state. The cross-section shown is parallel to a different side of the cartridge system than the cross-sections shown in FIGS. 1 to 5. In relation to FIGS. 1 to 5, this cross-section would extend perpendicular from top to bottom relative to the cross-sections shown there.

The cross-section extends through a first cartridge 52 with a second cartridge being arranged behind said cartridge 52 and therefore not being visible. All sectioned bodies are shown hatched in FIG. 6. The inside of the cartridge 52 contains a liquid or pasty starting component 54 for a mixing ware. The cylindrical inside space of the cartridges 52, which contains the starting component 54, is closed in the front (on the top in FIG. 6) through a closure 56 and on the back through a feed plunger 58. The closure 56 and the feed plunger 58 reside in a press-fit in the cartridge 52 and close the cartridge. The press-fit seals the inside of the cartridge 52 containing starting component 54 sufficiently such that seals on closure 56 and feed plunger 58 are dispensable.

A rotatable locking device 60 is arranged as cartridge head in a bracket (not shown) at the front end of the cartridge system, whereby the rotatable locking device 60 comprises a recess 62. FIG. 6 shows the locking device 60 in the open state in which the recess 62 forms the major part of a hollow space 62 for lowering the closure 56. When the locking device 60 is rotated differently, the walls of the locking device 60 ensure that the closure 56 cannot be lowered into the hollow space 62 such that the cartridge system can be used only in the state shown.

An opening 64 is provided in the locking device 60 and in the cartridge wall, the view onto which is depicted in FIG. 6, and can be closed and opened by means of the closure 56. A force acting on the feed plunger 58 is transmitted to the closure 56 by means of the starting components 54. In the position of the locking device 60 shown, the closure 56 is pushed past the opening 64 into the hollow space 62. Finally, the cartridge content 54 can flow from the cartridge 52 through the opening 64 into a mixing space situated downstream (not shown) where it is mixed with the other starting component from the second cartridge.

The locking device 60 is firmly connected to a dispensing tube 66 such that the dispensing tube 66 rotates along with the locking device 60. The mixing space is bordered, at least over regions thereof, through the locking device 60 or is provided to be situated therein entirely.

The locking device 60 is provided as a rectangular cylinder having a circular base surface, in which the recesses 62, the mixing space and the openings 64 as connections to the mixing space for each of the cartridges 52 are contained. Moreover, a feed-through to the dispensing tube 66 and ventilation openings (not shown) can be provided in the locking device 60. The locking device 60 can be rotated about its cylinder axis, as is indicated in FIG. 6 through the arrows on the left side, in order to transition the locking device 60 from the closed position to the open position (shown in FIG. 6). The locking device 60 can be provided in the form of a roller.

The locking device 60 provides additional safety against the feed plungers 58 being pushed-in inadvertently and the cartridge system being thus opened. In turn, one additional working step must be performed in order to render the cartridge system ready for use.

An inspection window 68 through which the closure 56 can be recognised in the lowered end position in the hollow space 62 is provided on the side. The inspection window 68 actually is situated above the cross-section shown and is therefore indicated by a dashed line. The inspection window 68 can be covered through a transparent plastic material such that it can be used exclusively to indicate the state of the cartridge system or the inspection window 68 is open and simultaneously serves as ventilation opening 68.

Accordingly, the cylindrical locking device 60 forms the front part of the cartridges 52 and is to be seen as a mobile part thereof.

The features of the invention disclosed in the preceding description and in the claims, figures, and exemplary embodiments, can be essential for the implementation of the various embodiments of the invention both alone and in any combination.

LIST OF REFERENCE NUMBERS 2, 52 Cartridge
4, 54 Starting component for the mixing ware
6, 56 Closure
8, 58 Feed plunger
10, 12 Seal
14 Stripping lip
16, 64 Opening
18 Mixing space
20, 62 Hollow space/recess
22 Cartridge head
24 Ventilation opening
26, 66 Dispensing tube
28 Static mixer
30 Thread
32 Indicator
34 Tube
60 Locking device
68 Ventilation opening/inspection window

What is claimed is:

1. A cartridge system for mixing and applying a mixing ware, comprising:
    at least two cartridges (2, 52) arranged parallel to each other and having an outlet opening,
    the cartridges (2, 52) each comprise cartridge walls with at least one opening (16, 64) that connects the cartridges (2, 52) to a mixing space (18),
    the cartridges (2, 52) each comprise a feed plunger (8, 58) for expelling starting components (4, 54) of the mixing ware from the cartridges (2, 52) through the at least one opening (16, 64) into the mixing space (18),
    each cartridge (2, 52) has at least one closure (6, 56), the at least one closure is shiftable in longitudinal direction of the cartridges (2, 52), from a starting position, wherein the at least one closure (6, 56) close the at least one opening (16, 64) of the cartridges (2, 52) to an end position, wherein the at least one closure at least partially opens the at least one opening (16, 64),
    wherein each of the at least two cartridges (2, 52) comprise a cylindrical hollow space (20, 62) for accommodating the at least one closure (6, 56),
    wherein the at least one closure (6, 56) is cylindrical in shape,
    wherein the cartridge includes a cartridge head (22) which defines the cylindrical hollow space (20, 62), the cartridge head (22) includes a ventilation opening (24, 68), and wherein, upon moving the at least one closure (6, 56) towards exposing the openings (16, 64), air escapes from the hollow space (20, 62).

2. The cartridge system according to claim 1, wherein at least one closure (6, 56) separate the hollow spaces (20, 62) from the cartridge (2, 52) filled with the starting components (4, 54).

3. The cartridge system according to claim 1, wherein the at least one closure (6, 56) is arranged in the cartridges (2, 52) in a press-fit.

4. The cartridge system according to claim 1, wherein the at least one closure (6, 56) is one of a compact body, a hollow body, or a hollow cylinder having at least one closed base surface.

5. The cartridge system according to claim 1, wherein the hollow space (20, 62) has an internal diameter that is equal to or larger than an external diameter of the corresponding closure (6, 56), and/or the hollow space is of a length of at least one-tenth of the height of the closure (6, 56).

6. The cartridge system according to claim 1, wherein each cartridge (2, 52) has at least one blocking organ arranged in the cartridge that limits the axial motion of the closure (6, 56) above the outlet opening.

7. The cartridge system according to claim 1, wherein the feed plunger (8, 58) in each cartridge (2, 52) is connected in a non-positive fit-manner to the closure (6, 56) of said cartridge (2, 52) by the starting component (4, 54) arranged in the cartridge (2, 52) such that a force acting on the feed plungers (8, 58) is transferred to the closures (6, 56) and the closures (6, 56) is transitioned from the starting position to the end position.

8. The cartridge system according to claim 1, wherein the feed plungers (8, 58) and closures (6, 56) are arranged in pairs, each in a tube (34), which contain one starting component (4, 54) each, wherein the tubes (34) are arranged in the cartridges (2, 52).

9. The cartridge system according to claim 1, wherein the mixing space (18) connected to a dispensing tube (26, 66) includes a removable static mixer (28).

10. The cartridge system according to claim 9, whereby the static mixer (28) extends into the mixing space (18).

11. The cartridge system according to claim 1, wherein the mixing ware is medical cement.

12. A cartridge system for mixing and applying a mixing ware, comprising:
    at least two cartridges (2, 52) arranged parallel to each other and having an outlet opening,
    the cartridges (2, 52) each comprise cartridge walls with at least one opening (16, 64) that connects the cartridges (2, 52) to a mixing space (18),
    the cartridges (2, 52) each comprise a feed plunger (8, 58) for expelling starting components (4, 54) of the mixing ware from the cartridges (2, 52) through the at least one opening (16, 64) into the mixing space (18),
    each cartridge (2, 52) has at least one closure (6, 56), the at least one closure is shiftable in longitudinal direction of the cartridges (2, 52), from a starting position, wherein the at least one closure (6, 56) close the at least one opening (16, 64) of the cartridges (2, 52) to an end position, wherein the at least one closure at least partially opens the at least one opening (16, 64),
    wherein each of the at least two cartridges (2, 52) comprise a cylindrical hollow space (20, 62) for accommodating the at least one closure (6, 56),
    wherein the at least one closure (6, 56) is cylindrical in shape,
    wherein at least one closure (6, 56) includes an optical indicator (32) arranged on the at least one closure, allowing to visualize the starting position and differentiating the starting position from the end position by at least one inspection opening (24, 68), or which projects from the cartridge (2, 52) through said at least one inspection opening (24, 68) when the closure (6, 56) is in the end position, whereby the inspection opening (24, 68) preferably also serves as the ventilation opening (24, 68).

13. A cartridge system for mixing and applying a mixing ware, comprising:
    at least two cartridges (2, 52) arranged parallel to each other and having an outlet opening,
    the cartridges (2, 52) each comprise cartridge walls with at least one opening (16, 64) that connects the cartridges (2, 52) to a mixing space (18),
    the cartridges (2, 52) each comprise a feed plunger (8, 58) for expelling starting components (4, 54) of the mixing ware from the cartridges (2, 52) through the at least one opening (16, 64) into the mixing space (18),
    each cartridge (2, 52) has at least one closure (6, 56), the at least one closure is shiftable in longitudinal direction of the cartridges (2, 52), from a starting position, wherein the at least one closure (6, 56) close the at least one opening (16, 64) of the cartridges (2, 52) to an end position, wherein the at least one closure at least partially opens the at least one opening (16, 64),
    wherein each of the at least two cartridges (2, 52) comprise a cylindrical hollow space (20, 62) for accommodating the at least one closure (6, 56),
    wherein the at least one closure (6, 56) is cylindrical in shape,
    wherein a rotatable locking device (60) is supported in a bearing in a bracket in the region of the cartridge head such as to be rotatable, wherein the locking device (60) is a rotationally symmetrical body having at least one cylindrical recess (62), wherein the locking device (60), forms at least one cartridge head (22) and the recess (62) of the locking device (60), in a first position, forms at least one part of one of the hollow spaces (62) for accommodating the closure (56) such that the closure (56) of said cartridge (52) is lowered into the hollow space (62) in the first position and cannot be lowered into the hollow space (62) in a second, rotated position of the locking device (60).

14. The cartridge system according to claim 13, wherein a dispensing tube (66) is arranged on the locking device (60) and, in the first position, is connected to the mixing space by the locking device (60), wherein the outlet opening of the mixing space is closed through the locking device (60) being in the second position.

* * * * *